United States Patent [19]
Butcher, Jr.

[11] Patent Number: 5,728,909
[45] Date of Patent: *Mar. 17, 1998

[54] METHOD OF CRACKING POLYMERIC MATERIALS CATALYZED BY COPPER

[75] Inventor: Jared A. Butcher, Jr., Athens, Ohio

[73] Assignee: Ohio University, Athens, Ohio

[*] Notice: The term of this patent shall not extend beyond the expiration date of Pat. No. 5,315,055.

[21] Appl. No.: 195,232

[22] Filed: Feb. 14, 1994

Related U.S. Application Data

[63] Continuation of Ser. No. 998,327, Dec. 30, 1992, Pat. No. 5,315,055.
[51] Int. Cl.$^6$ .................................................. C07C 17/00
[52] U.S. Cl. ...................... 585/241; 585/700; 585/752
[58] Field of Search .................................. 585/241, 700, 585/752

[56] References Cited

U.S. PATENT DOCUMENTS

| | | | |
|---|---|---|---|
| 3,996,022 | 12/1976 | Larsen | 585/241 |
| 4,108,730 | 8/1978 | Chen et al. | 585/241 |
| 5,315,055 | 5/1994 | Butcher, Jr. | 585/241 |

*Primary Examiner*—Glenn Caldarola
*Assistant Examiner*—Elizabeth D. Wood
*Attorney, Agent, or Firm*—Standley & Gilcrest

[57] ABSTRACT

The present invention is a method for depolymerizing or "cracking" polymeric materials. The method of the present invention may be used in the disposal and/or recycling of such materials. Products of the degradation of polymeric materials using the present method may be recycled or more easily treated for disposal. The present invention is a process for degrading, depolymerizing or "cracking" a polymeric material, otherwise amenable to cracking by alkali fusion, comprising the steps of:

(a) preparing a molten reaction mixture comprising:
  (i) a basic material;
  (ii) a source of copper; and
  (iii) said polymeric material; and
(b) maintaining said molten mixture at a temperature sufficient to reflux said molten mixture for sufficient time to depolymerize said polymeric material.

11 Claims, No Drawings

METHOD OF CRACKING POLYMERIC MATERIALS CATALYZED BY COPPER

This application is a continuation of application Ser. No. 07/998,327, filed Dec. 30, 1992, now U.S. Pat. No. 5,315,055.

TECHNICAL FIELD

The present invention is a method for depolymerizing or "cracking" polymeric materials. The method of the present invention may be used in the disposal and/or recycling of such materials. Products of the degradation of polymeric materials using the present method may be recycled or more easily treated for disposal.

BACKGROUND

In recent years there has been increased interest in both environmental protection and the conservation of both natural resources and synthetic materials through recycling.

One of the general classes of materials known to pose some of the greatest challenges to recyclers is synthetic polymers, such as plastics. This is largely due to the fact that their chemical nature materials makes them difficult to effectively and efficiently degrade to their constituent monomers, lower molecular weight oligomers, or other breakdown products, for reuse or safe disposal. The chemical nature of polymeric materials also make them difficult to handle, dispose of and/or recycle as their degradation products are often toxic or otherwise insulting to the environment.

Another factor making synthetic polymers difficult to recycle is their variety. Many degradation techniques may target depolymerization of only a limited number or type of polymeric materials, leaving others intact. Also, polymeric materials in the waste stream are often comingled with a wide variety of solid and liquid wastes which can foul recycling/disposal treatment processes. This factor can complicate attempts at large scale recycling of polymeric materials by requiring multiple process and/or separation steps.

In addition, synthetic polymeric materials, including polyethylene, polyvinylchloride, polystyrene, polypropylene and the like, make up a substantial portion of the waste generated by industry and municipalities. Accordingly, another aspect of the challenge to recycling or disposal of polymeric materials is the need to design recycling/disposal systems capable of functioning effectively on a scale sufficient to accommodate the volume and variety of polymeric materials in an industrial or municipal waste stream.

Beyond being able to render polymeric waste to disposable form, it is of course most desirable to be able to convert polymeric waste to reusable materials. In addition to being valuable as fuel, breakdown compounds of this type provide a ready feedstock for the preparation of detergents, lubricants and other, more valuable commodities. Likewise, depolymerization products can also be used in the preparation of new polymers, such as plastics.

Accordingly, it is desirable to be able to chemically degrade a wide variety of polymeric materials, particularly those classes of materials that constitute the greatest portion of waste polymeric materials generated in industrial or domestic settings.

It is also desirable to be able to render waste polymeric materials to a form amenable to reuse. This may mean producing degradation products which are both capable of being used as starting materials in the production of new materials and which are also in suitable form for such reuse, considering ease and safety of handling, demands of relative purity, etc.

Another beneficial characteristic in recycling/disposal processes is the ability to carry out the process in the presence of solid and liquid waste contaminants. Also, it is advantageous to be able to carry out recycling/disposal processes without the use of higher temperatures in the vapor phase (less than those needed for combustion), and without having to provide specialized atmospheres (e.g. absent oxygen), pressurized atmospheres, atmospheres using constant gas streams or specific pure gases or gas mixtures.

The many embodiments of the present invention make progress toward the accomplishment of the above objectives. In light of the present disclosure and/or the practice of the present invention, other advantages and/or the solution to additional problems, may become apparent to one skilled in the relative arts.

SUMMARY OF THE INVENTION

The present invention is a method useful in the recycling or disposal of many types of polymeric materials such as those plastics found in municipal and industrial waste streams and landfills. These materials include polyethylene, polystyrene, polypropylene and the like.

As to the treatment or recycling of polyethylene, it is known that the chemical degradation of polyethylene under reactive conditions known as "alkali fusion" yields a chemically active liquid hydrocarbon product mixture having a boiling range and chemical properties resembling kerosene or diesel fuel.

Alkali fusion has been historically discussed as a method in the classical analysis of organic compounds. It is well known because it has been applied to most natural products for the purpose of structure elucidation. However, it remains mysterious because the mechanism by which it operates has been, and remains, poorly understood. It has been applied to molecules containing all known functional groups, and extensive literature exists on the subject. One example of a use for alkali fusion is the preparation of oxalic acid from sawdust.

In general terms, alkali fusion can be described as the degradation of a polymeric material through the use of a molten basic material at high temperatures which can be generally characterized as those associated with pyrolytic conditions, i.e. 750° to 900° Fahrenheit. Many such processes involve the use of pressurized atmospheres, specific gas atmospheres (e.g. absent oxygen) or continuous gas flow through the reaction vessel.

The present invention represents an improvement over known "alkali fusion" methods. It has been found that the presence of a catalytic amount of copper allows the depolymerization of polymeric substances to be carried out at relatively low temperatures and permits such depolymerization to be carried out under air at atmospheric pressure.

In broadest terms, the present invention is a process for degrading, depolymerizing or "cracking" a polymeric material, otherwise amenable to cracking by alkali fusion, comprising the steps of:

(a) preparing a molten reaction mixture comprising:
  (i) a basic material;
  (ii) a source of copper; and
  (iii) said polymeric material; and
(b) maintaining said molten mixture at a temperature sufficient to reflux said molten mixture for sufficient time to depolymerize said polymeric material.

As used herein, the terms "depolymerization," "degradation" and "cracking" are all to understood as applied in the context of polymeric materials, and are intended to mean the breaking down of a polymeric material by the breaking of polymer-forming chemical bonds whereby the polymeric material is rendered to smaller polymeric subunits, oligomers, etc. and/or monomeric units, whether in gaseous, liquid and/or solid forms.

The term "basic material" is intended to mean any basic material capable of acting as a Lewis base. Although not limited by theory, basic materials appropriate for use in the method of the present invention include those materials which, when molten, generate hydroxide ions ($^-$OH) and/or hydroxy radical (·OH). Basic materials which may be used in the present invention include NaOH, KOH, $Na_2B_4O_7 \cdot 10H_2O$, $Na_3BO_3$, $Na_2SiO_3$, $K_2SiO_3$, and mixtures thereof. Other basic materials which may be used in the present invention include basic materials used in so-called alkali fusion reactions. When used to depolymerize polyethylene, a mixture of NaOH and KOH present in weight ratio of about 1:1 is preferred.

As used herein the term "source of copper may be any source of copper, regardless of its oxidation state. For example, sources of copper which may be used in the present invention include metallic copper or copper (II) such as in the form of copper oxide (CuO). When used to depolymerize polyethylene, copper metal (e.g. supplied in the form of powder or even in the form of a copper reaction vessel) or copper (I) oxide is preferred. The copper used in the method of the present invention, when initially in one oxidation state (e.g. zero, one, or two), may be converted to a different oxidation state in the environment of the depolymerization reaction of the present invention. Accordingly, the present invention is not limited to the original or ultimate oxidation state of the copper used therein.

It is also preferred that the copper source be in a physical form adapted to best react in the reaction of the present invention, such as a granulated or powdered form.

The source of copper need only be present in an amount sufficient to supply a catalytic amount of copper. Typical amounts of copper are on the order of about 5% by weight of the molten reaction mixture, although a given reaction may be found to be operative with lesser amounts of copper. Accordingly, the present invention in its broadest form is not limited to a specific amount or range-of amounts of copper. Rather an effective catalytic amount of copper may be ascertained without undue experimentation in light of the present disclosure.

As used herein "polymeric material(s)" may include any thermoplastic or thermosetting polymeric material including polyethylene, polystyrene, polyvinylchloride, and polypropylene. It has been found that the method of the present invention does not operate on vulcanized rubber.

The time/temperature conditions under which the molten reaction mixture is allowed to react can generally be described as those sufficient to bring about depolymerization. The extent and degree of depolymerization may vary with the time/temperature parameters as well as with the type(s) of polymeric materials to which the method is applied. However the temperatures sufficient to bring about depolymerization under normal circumstances are those sufficient to bring about reflux of the reaction mixture. Such temperatures, as measured in the vapor phase over the reaction mixture, are generally in the range of from about 100° C. to about 500° C.; preferably in the range of from about 100° C. to about 350° C.; and normally between about 150° C. and about 250° C. The reaction time of the present invention may of course be varied depending upon the type(s) of polymeric materials to which the method is applied and the degree of depolymerization desired. These parameters can be readily derived in light of the present disclosure. Accordingly, the present invention in broadest terms is not limited to any particular reaction temperature, reaction time or reaction time/temperature combination, except as conforms to the parameters outlined herein and exemplified by the working examples. In many cases, breakdown products in the form of a distillate can be drawn from the reaction mixture, so the reaction can be run as long as product is being produced.

The reaction time also has been found to vary with the age and condition of the catalyst. It has been found in some instances that the catalyst loses efficiency in subsequent reaction runs. Accordingly, it is preferred that the efficiency of the reaction be monitored and fresh catalyst used as required. The need for fresh catalyst will be apparent from the reaction efficiency and can be determined by one of ordinary skill without undue experimentation.

DETAILED DESCRIPTION OF THE PREFERRED EMBODIMENTS

The following presents a detailed description of the preferred embodiments of the present invention, which are presently considered the best mode of practicing the invention.

Plastics used in the procedures of the examples given below were obtained from household waste. They include high density polyethylene (HDPE) obtained as milk jugs (transparent, colorless), detergent or cleaning products (opaque), and oil bottles (green); polypropylene (PP) obtained from food containers; polystyrene (PS) obtained as plastic peanuts; and polyvinyl chloride (PVC) obtained as plastic tubing.

The plastic articles were cut into chips about 8 mm square by using either a mechanical cutter (scissors) or an electrical cutter composed of an array of hot nichrome wires. The bottles were drained, but no attempt was made to clean them or to remove the labels. The basic material used was commercial sodium hydroxide and commercial potassium hydroxide pellets, except where indicated.

These NaOH and KOH pellets were mixed with traces of cuprous oxide ($Cu_2O$) in the ratio of 10:10:1 (NaOH:KOH:$Cu_2O$), although the ratio was not critical to the success of the cracking process.

In general, the pellets of base (with copper) and the plastic substrate could be mixed and heated together, but a superior result was obtained when plastic chips were added to an agitated NaOH/KOH melt, commonly referred to as alkali fusion reaction conditions. It was important to note that in either case, the mixture of plastic and base was heated at or near the melting point of the base (i.e. about 210° C.) for sufficient time (e.g. period of between 5 and 20 minutes) for the reaction to commence, as evidenced by liquid refluxing at or below 200° C.

At this point, condensate was collected at a convenient rate (1–2 drops per second) and stronger heating was applied as necessary. In these examples, product was not normally collected above 250° C., so the heat was moderated to maintain the temperature of the escaping vapor at or below this point. Rapid or excessive heating was avoided as this resulted in incomplete cracking of the plastic as evidenced by the presence of high melting wax in the condensate, and/or by polymer build-up in the cool portions of the distillation apparatus.

EXAMPLE 1

Green HDPE plastic chips (300 g) from oil plastic motor bottles were cracked in batches of 50 g each in a 400 mL copper vessel to yield about 150 mL of distilled hydrocarbons.

A 400 mL copper vessel was charged with NaOH pellets (11.8 g), KOH pellets (11.8 g) and $Cu_2O$ (0.8 g) and heated in a low flame with agitation until the mixture had melted. The vessel was then filled with plastic chips (about 45–50 g), attached to a PYREX® distillation apparatus consisting of a distillation adapter equipped with a 350° C. thermometer, a water-cooled condenser, a take-off adapter equipped with a side-arm, and an appropriate receiver (50 mL), and placed in an active hood. The reaction vessel was then heated gently over a low flame until refluxing vapor was evident in the glass portion of the apparatus (about 20 minutes) and then the flame was increased as needed to maintain a distillation rate of 1–2 drops per second.

Uncondensed hydrocarbon vapors emitted from the side-arm of the take-off adapter present a potential fire hazard. These should be vented far from the flame.

Distillation commenced at 160° C. as a mixture of hydrocarbons and water, and then the temperature rose to 230° C. where the bulk of the product (about 25 mL) was collected. The temperature rose rapidly to 250° C. after most of the hydrocarbon had distilled, and if it remained unchecked, a wax would distill above 250° C. and collect in the condenser. This wax, if present, was removed from the condenser and combined with the plastic chips used in subsequent batches. The apparatus was cooled to ambient temperature and a fresh supply of plastic chips was added and the procedure repeated until the catalyst was no longer active (six batches of 50 g each). At that point, the reaction vessel was emptied by pouring the residual molten alkali fusion mixture into 2 liters of water. Splattering and steam present a safety hazard, so precautions should be taken in this regard. The black wax (50 g) was then collected by filtration. Yield of liquid hydrocarbons was 50% (150 g) as a pale green liquid, the yield of wax was 16% (50 g) and the yield of gases was not measured in this experiment.

EXAMPLE 2

Colorless HDPE chips (10 g) from plastic milk jugs was liquified in a 50 mL copper vessel to yield 6.7 g of hydrocarbons consisting of a mixture of alkanes, terminal alkenes (α-olefins) and internal alkenes.

In a 50 mL copper vessel were placed NaOH (1 g) and KOH (1 g) and colorless HDPE chips (5 g). This assembly was attached to a standard PYREX® distillation apparatus by means of a 4" fractionating tube securely held to the copper reaction vessel by spring clips. Gentle heating with either a free flame, or a sand bath causes vapor to reflux in the fractionating tube after 10–12 minutes at or below 150° C. After the induction period, the heat was increased as necessary to distill the hydrocarbons at a rate of 1–2 drops per second. Fractions were taken at 1 mL intervals and analyzed. Once the temperature of the vapor reached 250° C., heating was suspended and additional plastic chips were added through the 24/40 joint located between the fractionation tube and the rest of the distillation apparatus. Heat was applied and the procedure was repeated as necessary to consume 10 g of plastic. The accumulated fractions revealed no significant difference in composition which indicated that a cracking process occurred continuously during the distillation, and the product yield (6.7 g, 67%) Was relatively constant for sample sizes ranging from 1 g to 25 g without additional catalyst being added. The residue present in the reaction vessel at the end of the reaction consisted of alkali comingled with traces of copper salts and very little wax or other organic (burnable) residue. No attempt was made to measure the volume of non-condensable gases, but ignition established that they were formed. It is important to be certain that the opening to the distillation apparatus is properly vented and kept away from the open flame at all times to avoid the possibility of fire.

This procedure has been repeated using white, yellow, and green HDPE. In all cases, the product mixture was identical.

EXAMPLE 3

Colorless HDPE (1 g) was cracked by using commercial 50% NaOH at reflux in a copper reaction vessel in <30% yield.

In a clean 50 mL copper vessel, containing no trace of organic residue, were placed 50% aqueous NaOH (5 mL) and 2 g of clean dry chopped HDPE from milk jugs. The apparatus was assembled as described in Example 2 and heating was commenced. After a period of reflux (15 minutes), yellow wax-like residue was detected in the liquid and at that point, a rudimentary form of steam distillation was initiated (i.e. water was added drop wise at a rate equal to the rate at which the distillation occurred). The organic and aqueous mixture of products was collected (50 ml) and the aqueous phase was removed by decantation. The wax that remained (about 0.5 g) was taken up in dichloromethane and analyzed. This analysis showed that the product in this case was a mixture of alkanes only, and those being of higher molecular weight than the product observed in either of the previous Examples described above.

EXAMPLE 4

Colorless HDPE (1 g) was cracked by using alkali fusion in a glass vessel.

A disposable glass vessel was charged with NaOH (0.5 g) and KOH (0.5 g) and $Cu_2O$ (trace; about 0.1 g) and heated over a free flame until the alkali melt formed and all of the copper oxide had dissolved to give a blue solution. Caution should be taken as extensive heating of molten alkali in PYREX® glass vessels will cause leakage due to irreversible damage to the glass. Plastic chips were then added and heating was resumed. After an induction period, the blue color was dispelled and a red precipitate, presumed to be finely divided copper metal, precipitated with simultaneous "foaming" around the edges of the plastic chips. Vapor collected after this point had the composition reported in Example 2, above.

EXAMPLE 5

Polypropylene was cracked under alkali fusion conditions.

Polypropylene food containers were cut into chips and substituted for HDPE as described in Example 3. The temperature range over which the product distilled was higher in that the product was collected between 300° C. and 350° C. No low boiling fraction was observed. The yield ranged between 40–50% on a 5 g scale.

EXAMPLE 6

Polystyrene was cracked under alkali fusion conditions.

Polystyrene from so-called "plastic peanuts" was subjected to the conditions described in Example 3. The temperature over which the product distilled ranged between 110° C. and 200° C. and the yield exceeded 60% (unoptimized) on a 5 g scale. A relatively large amount of water was observed in the condensate.

EXAMPLE 7

Commingled plastic was cracked under alkali fusion conditions.

A mixture of plastics composed of polyethylene chips from milk jugs and polyvinylchloride chips from plastic water pipe were subjected to the reaction conditions described in Experiment 3. No inhibition of the cracking process was observed, but the yield was generally lower, ranging between 40–50% depending on the quantity of PVC used.

Results

The first conclusion evident from the experiments above was that the colorant additives present in polyethylene that render it opaque do not interfere with the process of the present invention described herein. Additives present in oil residue do have a damaging effect and were not cracked under the conditions used in the experiments done to date. Similarly, the presence of other plastics does not alter the chemistry of polyethylene in any significant way, and polyvinyl chloride was no exception. The breakdown products from different plastics boil at different temperatures and this effectively alters the yield of product isolated in a given distillation temperature range.

The basic material needed to bring about the reaction of the present invention was insensitive to inorganic impurities such as silicates and borates present in glass. In fact, intentional addition of borax and sodium silicate to the reaction mixture had no significant effect on the production of liquid distillate, and pure borax catalyzes the plastic cracking under the conditions described above. Although not limited by theory, this suggests that borax could be a source for the hydroxide ion or radical implicated as being central to the mechanism of the reaction.

The presence of water leads to higher molecular weight alkane fragments. This suggests that water was necessary for the reaction leading to hydrocarbons in general, and this is consistent with the data once it is remembered that commercial grade NaOH and KOH retain water in their solid structure. Experiments designed to reduce the concentration of water in the melt led to the formation of more short-chain alkenes, thus establishing that changing water concentration is a means for controlling the composition of the product mixture.

The need for copper ion or other reducible species to be present in the reaction mixture was established via the use of a negative control. Reaction vessels composed of high nickel stainless steel and Sterling silver were employed to crack polyethylene under conditions similar to those described above but which did not involve copper ion in any form. The result was low yield (<20%) in both cases. Addition of $Cu_2O$ to the melt in a silver vessel caused an immediate reaction and efficient cracking was obtained as described in Example 3. Without the addition of copper the reaction rate was unmeasurably slow even at extreme temperature. This observation was one of the first to implicate copper in the reaction mechanism since traditional wisdom indicates that the nature of the reaction vessel has no significant effect on the products of alkali fusion, and that silver vessels are preferred since they are only slowly attacked by molten alkali.

Another of the initial clues to the importance of copper ion in the alkali melt came through the observation that certain glass vessels were superior to others in catalyzing in the process. Since iron and copper are common impurities in glasses, these were investigated, but only copper showed any measurable effect. This was consistent with the observation that a high nickel stainless steel vessel containing traces of iron proved to be inferior to a copper reaction vessel. Flakes of CuO scraped off the copper reaction vessel proved to be sufficient to catalyze the plastic cracking reaction in a silver reaction vessel.

The need for molten alkali was established by conducting experiments in clean glass apparatus. Polyethylene was melted and heated in air and cracking ensued at temperatures in excess of 400° C. and coated the interior of the vessel with a film of wax. The addition of NaOH pellets to the molten plastic caused an immediate frothing and foaming and cracking initiated. The yield obtained by this method was inferior to any of the examples specified above, but it did establish the utility of molten alkali. In instances where the cracking reaction had stopped during the procedure described in Example 3 the addition of NaOH and KOH pellets has been used successfully to restart and extend the plastic cracking reaction.

The importance of air in this procedure should not be overlooked. In contrast to many published procedures in which oxygen was excluded from the reaction chamber during the cracking process, no attempt was made to remove or exclude oxygen in this case.

Although not limited to a mechanistic theory, it is believed that the mechanism involves cycling the oxidation state of copper from +1 to zero (0) or +2 to zero (0) and in this way copper ion provides a sink for an electron from hydroxide ion. Oxidation of copper with atmospheric oxygen provides a convenient rationalization for the presence of oxidized forms of copper and it seems to explain the catalytic nature of the alkali mixture containing them.

Characteristics of the product

The primary analytical tool used in studying the nature of the products obtained from the method of the present invention has been GCMS. These data disclose the number of components and their relative concentrations.

NMR has been used to detect the presence of terminal and internal olefins, and to search for branching in the alkyl chain. No branching was detected in the alkyl chains of products from polyethylene, but the products from other plastics, such as polypropylene were more complicated. The product formed from the depolymerization of PVC was not characterized.

In view of the foregoing disclosure and representative Examples, it will be within the ability of one skilled in the chemical or chemical engineering art to make modifications and variations to the disclosed embodiments, including the use of equivalent materials and process steps without departing from the spirit of the invention.

What is claimed is:

1. A method of depolymerizing a polymeric material, said method comprising the steps:
   (a) preparing a molten mixture comprising:
      (i) a basic material capable of producing hydroxide ions;
      (ii) a source of copper selected from the group consisting of copper metal, univalent copper, divalent copper, and mixtures thereof; and
      (iii) said polymeric material selected from the group consisting of thermoplastic polymeric material, thermosetting polymeric material and mixtures thereof; and (b) maintaining said molten mixture at a temperature sufficient to reflux said molten mixture so as to produce a vapor and at a temperature, as measured from said vapor, below about 250° C. for sufficient time to depolymerize said polymeric material.

2. A method according to claim 1 wherein said basic material is selected from the group consisting of NaOH, KOH, $Na_2B_4O_7 \cdot 10\ H_2O$, $Na_3BO_3$, $Na_2SiO_3$, $K_2SiO_3$, and mixtures thereof.

3. A method according to claim 2 wherein said basic material comprises NaOH and KOH.

4. A method according to claim 2 wherein said basic material comprises $Na_2B_4O_7\ 10H_2O$ and NaOH.

5. A method according to claim wherein said source of copper is present an mount sufficient to provide a concentration of cooper of at least 5% by weight of said molten mixture.

6. A method according to claim 1 wherein said source of copper is copper metal.

7. A method according to claim 1 wherein said molten mixture is maintained in a reaction vessel comprising copper metal during step (b).

8. A method according to claim 1 wherein said source of copper is copper (I) oxide.

9. A method according to claim 1 wherein said polymeric material is thermoplastic polymeric material.

10. A method according to claim 1 wherein step (b) is carried out under air at atmospheric pressure.

11. A method according to claim 9 wherein said thermoplastic polymeric material is selected from the group consisting of polyethylene, polystyrene, polyvinylchloride, and polypropylene and mixtures thereof.

* * * * *

UNITED STATES PATENT AND TRADEMARK OFFICE
CERTIFICATE OF CORRECTION

PATENT NO. : 5,728,909
DATED : Mar. 17, 1998
INVENTOR(S) : Jared A. Butcher, Jr.

It is certified that error appears in the above-identified patent and that said Letters Patent is hereby corrected as shown below:

In column 5, line 66, please delete the word "Was" and replace it with -- was --.

In column 9, line 15, please delete the word "mount" and replace it with -- amount --.

Signed and Sealed this

Sixteenth Day of June, 1998

Attest:

BRUCE LEHMAN

Attesting Officer

Commissioner of Patents and Trademarks